United States Patent [19]

McEntire

[11] 4,259,259
[45] Mar. 31, 1981

[54] PREPARATION OF β-AMINOPROPIONAMIDES

[75] Inventor: Edward E. McEntire, Austin, Tex.

[73] Assignee: Texaco Development Corp., White Plains, N.Y.

[21] Appl. No.: 94,416

[22] Filed: Nov. 15, 1979

[51] Int. Cl.³ .......................................... C07C 102/06
[52] U.S. Cl. ............................. 564/137; 260/326.25; 544/86; 544/96; 546/186; 546/208; 546/209; 564/197
[58] Field of Search .......... 260/561 A, 561 R, 326.25; 252/443; 546/208, 209, 186; 544/86, 96

[56] References Cited

U.S. PATENT DOCUMENTS

| | | | |
|---|---|---|---|
| 2,451,436 | 10/1948 | Erickson | 260/561 N |
| 3,145,195 | 8/1964 | Tsou | 260/561 A |
| 3,924,046 | 12/1975 | Ribka et al. | 260/561 N |
| 4,031,138 | 6/1977 | Nieh et al. | 260/561 N |
| 4,134,916 | 1/1979 | Moss et al. | 260/561 N |

Primary Examiner—Arthur P. Demers
Attorney, Agent, or Firm—Carl G. Ries; Robert A. Kulason; James L. Bailey

[57] ABSTRACT

Covers a process for the preparation of a β-aminopropionanide of the formula

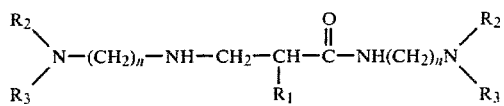

wherein $R_1$ is H or methyl, n is an integer of 2 to 6 and $R_2$ and $R_3$, taken singly are hydrogen or lower alkyl groups containing 1 to 4 carbon atoms or $R_2$ and $R_3$, taken jointly are combined with the nitrogen atom to form a heterocyclic group selected from the groups consisting of morpholine, pyrrolidine and piperidine ring groups; which process comprises reacting in the presence of an alkali or alkaline earth metal salt of a strong acid having a $pK_a$ of less than about 2.0 acting as a catalyst a tertiaryaminoalkyl amine of the formula:

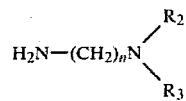

where $R_2$, $R_3$ and n are as above with an acrylic or methacrylic compound of the formula:

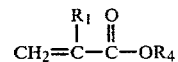

where $R_1$ is as above and $R_4$ is lower alkyl and recovering said β-aminopropionamide.

9 Claims, No Drawings

PREPARATION OF β-AMINOPROPIONAMIDES

BACKGROUND OF THE INVENTION

1. Field of the Invention

The present invention relates to a catalytic chemical process for making β-aminopropionamides. Such compounds are particularly useful derivatives in further preparing cationic vinyl monomers useful in preparing flocculants, adhesion promoters, oil soluble dispersions, epoxy curing agents and ion exchange resins.

2. Description of the Prior Art

It is well-known that amines will react with acrylic or methacrylic esters to form β-aminopropionamides. Thus, for example, certain β-aminopropionamides compounds can be made by reacting dialkyl amine compounds with an acrylic acid or ester compound, as described in the article by J. G. Erickson, "The Preparation and Stabilities of Some β-dialkylaminopropionamides", J. Am. Chem. Soc. 74, 6281-82 (1952).

Aminolysis of esters is also described by J. F. Bunnett and G. T. Davis, J. Am. Chem. Soc. 82, 665 (1960) and H. T. Openshaw and M. Whittaker, J. Chem. Soc. 89, (1969). Other processes leading to compounds of this type are set out in U.S. Pat. Nos. 2,451,436; 2,529,838; 2,649,438; and 3,652,671.

As set out in U.S. Pat. Nos. 2,719,175 and 2,719,178 the resultant β-aminopropionamides can then be broken down by heat to give monomeric compounds.

However, normally the reaction between an amine and an acrylic or methacrylic ester will proceed only slowly at moderate temperatures. One can elevate the temperature to complete the reaction and form the desired propionamide but then side reactions become significant.

In order to promote the reactions between esters and amines use of certain compounds have been suggested. For example, in the article by H. L. Bassett and C. R. Thomas, J. Chem Soc. 11, 1188 (1954) the use of stoichiometric quantites of an alkylmagnesium halide has been described. While such compounds have been found to act as an aid in forming amides, it was also found that catalytic quantities were not effective here. In yet another route in producing acrylamides from acrylic esters and amides the use of lithium hydroxide and magnesium methoxide as catalysts were proposed (German Pat. No. 1,164,397).

However to date no simple method has been found to form β-aminopropionamides from acrylic or methacrylic esters and the appropriate amines, which can be run at relatively low reaction temperatures, and which results in few side products compared to the prior art. Some catalysts, for example, in this area may catalyze the desired reaction, and likewise promote undesired side reactions.

It would therefore be an advantage in the art to provide a new catalytic method for preparing β-aminopropionamides, which reaction could be run at relatively low reaction temperature and would produce few quantities of undesired side products.

SUMMARY OF THE INVENTION

The present invention is an improved catalytic process for the preparation of β-aminopropionamides of the formula:

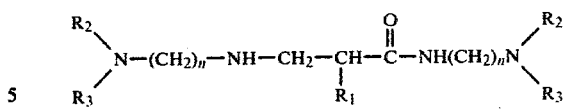

wherein $R_1$ is H or methyl, n is an integer of 2 to 6 and $R_2$ and $R_3$, taken singly are hydrogen or lower alkyl groups containing 1 to 4 carbon atoms or $R_2$ and $R_3$, taken jointly when combined with the nitrogen atom form a heterocyclic group selected from the group consisting of morpholine, pyrollidine and piperidine ring groups; which process comprises reacting in the presence of an alkali or alkaline earth metal salt of a strong acid having a $pK_a$ of less than about 2.0 acting as a catalyst a tertiaryaminoalkyl amine of the formula.

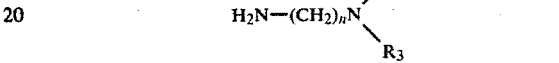

where $R_2$, $R_3$ and n are as above with an acrylic or methacrylic compound of the formula:

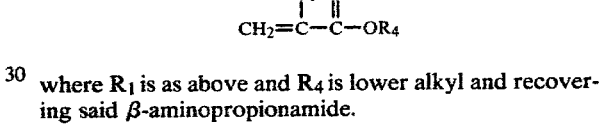

where $R_1$ is as above and $R_4$ is lower alkyl and recovering said β-aminopropionamide.

DETAILED DESCRIPTION OF THE INVENTION

The inventive process can be carried out batch-wise or in a substantially continuous procedure. Usually a molar excess of a tertiary-aminoalkylamine is combined with the acrylic or methacrylic acid ester compound, and the mixture is heated at a temperature within the range of 20°–200° C., most preferably 60°–140° C.

Most often at least two moles of the amine are utilized per mole of ester, and more often to drive the reaction to completion an excess greater than two moles of amine is employed. This insures maximum formation of the corresponding β-aminopropionamide compound. There is no criticality in the maximum amount of amine compound employed other than practical considerations of subsequent excess unreacted amine removal from the reaction mixture. Normally, the reaction product is formed within a time period of about ¼ to 24 hours, more often 0.5–10 hours. The amount of reaction time depends upon the particular starting materials employed and temperatures employed. The corresponding β-aminopropionamide reaction product can then be separated from the reaction mixture, which usually also contains alcohols and excess unreacted amine compound, if desired, by conventional distillation procedures. However, the inventive process is equally applicable to the continuous running of the entire reaction mixture, for the alcohol of reaction and excess unreacted amine do not adversely effect the process.

Reaction may also be effected at atmospheric, subatmospheric or superatmospheric pressures.

Tertiary aminoalkyamines which are especially useful in the practice of the present invention include: 3-dimethylaminopropylamine; 2-dibutylaminoethylamine; 4-(aminopropyl)morpholine; 3-diethylaminopropylamine; 2-dimethylaminoethylamine; 1-(aminopropyl)piperidine; and 4-(aminoethyl)-morpholine. Most preferably, 3-dimethylaminopropylamine is employed.

$R_2$ and $R_3$ when both alkyl are most preferable $C_1$–$C_4$ lower alkyl such as isopropyl and t-butyl. When $R_2$ is $=$H then $R_3$ is most preferably isopropyl, isobutyl, or t-butyl or other such branched lower alkyl. Radicals $R_2$ and $R_3$ may be extended to include up to about $C_6$ alkyl and branched alkyl.

$R_2$ and $R_3$ may contain other substituents of the non-interfering type such as tertiary amino, hindered amino, aryl, alkaryl, ether linkages, etc. The alkyl group may contain any substituent of this type which is inert to the reaction conditions in that the expected products are derived.

Particular acrylic acid or methacrylic acid ester compounds useful as reactants in the invention include: methyl acrylate, methyl methacrylate, ethyl acrylate, and ethyl methacrylate. Methyl acrylate and methyl methacrylate are preferred.

The amount of alkali or alkaline earth metal catalyst utilized may vary over a wide range. Usually based on the total weight of the reactants the catalyst is used in an amount ranging from about 0.01 up to about 10% by weight. More often the catalyst is employed in the range of 0.1–5 weight % based on total reactant weight present.

Any alkali or alkaline earth metal salt of a strong acid having a $pK_a$ of about 2.0 or less is useful in the invention as a catalyst in promoting the amidification reaction, such as the halides, nitrate, perchlorate and fluoroborate salts. Preferred alkali metal halides are lithium and sodium halides with lithium being most preferred such as lithium iodide. Preferred alkaline earth metal halides are magnesium, barium and calcium with magnesium and barium being most preferred such as the chloride and iodide forms. Preferred nitrate salts are those of magnesium and calcium.

The following examples are for purposes of illustration of the invention and are not intended to be limiting thereof.

EXAMPLE I

To a 500 ml flask equipped with a magnetic stirrer, thermometer, and nitrogen atmosphere were charged 204 g 3-(dimethylamino)propyl amine and 3.0 g anhydrous lithium iodide. The mix was heated to 80° C., during which time the lithium iodide dissolved. Methyl methacrylate, 100 g, was added in one portion. The reaction mixture was heated 3 hours at 80° C., then sampled, the catalyst remaining soluble.

Gas liquid chromatography analysis revealed the following area percent data:

| Compound | Area Percent | |
|---|---|---|
| methanol | 3.1 | |
| methyl methacrylate | 0.9 | |
| DMAPA | 34.1 | (Dimethylaminopropylamine) |
| P-Ester | 49.1 | (3-(3-dimethylaminopropylamino)-2-methyl-propionate, methyl ester) |
| DMAPMA | 3.4 | (N-(3-dimethylaminopropyl)methacrylamide) |
| P-Amide | 8.2 | (N-(3-dimethylaminopropyl)-3(3-dimethyl-aminopropyl)amino-2-methyl propionamide |

This data corresponds to a 9.2% yield of propionamide and to a 30% methanol yield.

EXAMPLES 2–9

The following experiments were conducted in a manner similar to Experiment 1, also with 0.022 moles of catalyst. The results are summarized by the gas-liquid chromatography data reduced to % yield $$\left(\frac{\text{actual yield}}{\text{theoretical yield}} \times 100\right).$$

Table I

| Experiment No. | Catalyst | Propionamide % Yield | Methanol % Yield |
|---|---|---|---|
| 2 | LiCl | 6.7 | 16.2 |
| 3 | $MgCl_2$ | 20.5 | 43.8 |
| 4 | $MgBr_2$ | 12.9 | 18.1 |
| 5 | $LiI\text{-}3H_2O$ | 17.3 | 39.5 |
| 6 | NaI | 2.7 | 7.6 |
| 7 | $MgI_2$ | 29.2 | 58.9 |
| 8 | $CaI_2$ | 6.3 | 16.2 |
| 9 | $BaI_2 2H_2O$ | 26.6 | 60.0 |

MMA-methyl methacrylate
P. Amide =
$(CH_3)_2NCH_2CH_2CH_2NHCH_2CH(CH_3)CONHCH_2CH_2CH_2N(CH_3)_2$

EXAMPLE 10

An experiment performed in a manner identical to Example I above without any catalyst showed only 0.1% yield of the product propionamide, with only 1.2% yield of methanol.

Obviously, many modifications and variations of the invention as here-in-before set forth may be made without departing from the spirit and scope thereof, and, therefore, only such limitations should be imposed as are indicated in the claims.

The invention is hereby claimed as follows:

1. A process for the preparation of a β-aminopropionamide of the formula

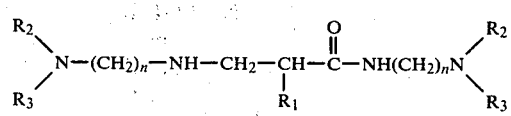

wherein $R_1$ is H or methyl, n is an integer of 2 to 6 and $R_2$ and $R_3$, taken singly are hydrogen or lower alkyl groups or $R_2$ and $R_3$, taken jointly when combined with the nitrogen atom form a heterocyclic group selected from the group consisting of morpholine, pyrrolidine and piperidine ring groups, which process comprises reacting in the presence of an alkali or alkaline earth metal salt of a strong acid having a $pK_a$ of about 2 acting as a catalyst, a tertiaryaminoalkyl amine of the formula.

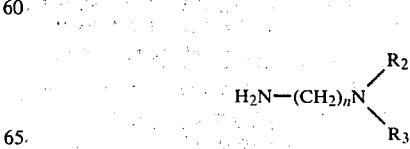

where $R_2$, $R_3$ and n are as above with an acrylic or methacrylic compound of the formula:

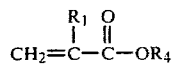

where $R_1$ is as above and $R_4$ is lower alkyl and recovering said β-aminopropionamide.

2. The process of claim 1 where $R_2$ and $R_3$ are methyl.
3. The process of claim 2 where n=3.
4. The process of claim 3 where $R_1$ is methyl.
5. The process of claim 4 where $R_4$ is methyl.
6. The process of claim 1 which is run at a temperature of 20°–200° C.
7. The process of claim 1 wherein said temperature range is 60°–140° C.
8. The process of claim 1 wherein said catalyst is a magnesium calcium or barium halide.
9. The process of claim 1 wherein said catalyst is a lithium halide.